US009262864B2

(12) United States Patent
Rohaly et al.

(10) Patent No.: US 9,262,864 B2
(45) Date of Patent: *Feb. 16, 2016

(54) SYNCHRONIZED VIEWS OF VIDEO DATA AND THREE-DIMENSIONAL MODEL DATA

(71) Applicant: 3M INNOVATIVE PROPERTIES COMPANY, St. Paul, MN (US)

(72) Inventors: Janos Rohaly, Concord, MA (US); Robert N. Nazzal, Waltham, MA (US); Edward K. Tekeian, Cambridge, MA (US); Ilya A. Kriveshko, Boxborough, MA (US); Eric B. Paley, Somerville, MA (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/487,371

(22) Filed: Sep. 16, 2014

(65) Prior Publication Data
US 2015/0002509 A1    Jan. 1, 2015

Related U.S. Application Data

(63) Continuation of application No. 12/666,464, filed as application No. PCT/US2008/068522 on Jun. 27, 2008, now Pat. No. 8,866,883.

(60) Provisional application No. 60/947,009, filed on Jun. 29, 2007.

(51) Int. Cl.
| | |
|---|---|
| *G06T 17/10* | (2006.01) |
| *H04N 13/00* | (2006.01) |
| *G06T 15/10* | (2011.01) |
| *A61C 9/00* | (2006.01) |

(Continued)

(52) U.S. Cl.
CPC .............. *G06T 17/10* (2013.01); *A61C 9/0053* (2013.01); *G06F 3/04815* (2013.01); *G06F 3/04847* (2013.01); *G06T 15/10* (2013.01); *H04N 5/14* (2013.01); *H04N 13/00* (2013.01); *H04N 13/0055* (2013.01)

(58) Field of Classification Search
CPC .............. A61C 9/0053; G06F 3/04815; G06F 3/04847; H04N 13/00; H04N 13/0055; H04N 5/14; G06T 15/10; G06T 17/10; G06T 17/20; G06T 19/00; G06T 17/00; G06T 17/005
USPC ............................................. 345/420; 348/43
See application file for complete search history.

(56) References Cited

U.S. PATENT DOCUMENTS

| | | |
|---|---|---|
| 4,846,577 A | 7/1989 | Grindon |
| 5,175,616 A | 12/1992 | Milgram |

(Continued)

FOREIGN PATENT DOCUMENTS

| | | |
|---|---|---|
| WO | WO 2004/100067 | 11/2004 |
| WO | WO 2007/103918 | 9/2007 |

*Primary Examiner* — Shan Elahi

(57) ABSTRACT

Video data acquired during a three-dimensional scan of dentition provides a source of still images that can be displayed alongside a rendered three-dimensional model of the dentition, and the two views (model and still image) may be synchronized to provide a common perspective of the model's subject matter. This approach provides useful visual information for disambiguating surface features of the model during interactive model processing steps such as marking a margin of a prepared tooth surface for a restoration.

20 Claims, 6 Drawing Sheets

(51) Int. Cl.
*G06F 3/0481* (2013.01)
*G06F 3/0484* (2013.01)
*H04N 5/14* (2006.01)

(56) References Cited

U.S. PATENT DOCUMENTS

| | | | | |
|---|---|---|---|---|
| 5,850,352 | A * | 12/1998 | Moezzi et al. | 345/419 |
| 6,409,504 | B1 * | 6/2002 | Jones et al. | 433/24 |
| 6,604,527 | B1 * | 8/2003 | Palmisano | 128/848 |
| 6,674,461 | B1 | 1/2004 | Klapman | |
| 6,974,323 | B2 * | 12/2005 | Weigl et al. | 433/223 |
| 7,077,646 | B2 * | 7/2006 | Hilliard | 433/6 |
| 7,110,594 | B2 * | 9/2006 | Jones et al. | 382/154 |
| 7,247,021 | B2 * | 7/2007 | Jones et al. | 433/213 |
| 7,474,932 | B2 | 1/2009 | Geng | |
| 8,866,883 | B2 * | 10/2014 | Rohaly et al. | 348/43 |
| 2002/0064759 | A1 * | 5/2002 | Durbin et al. | 433/213 |
| 2002/0102009 | A1 * | 8/2002 | Jones et al. | 382/100 |
| 2003/0033151 | A1 * | 2/2003 | Vozick et al. | 704/275 |
| 2003/0207235 | A1 * | 11/2003 | der Zel | 433/223 |
| 2004/0218039 | A1 * | 11/2004 | Cooper | 348/66 |
| 2004/0222945 | A1 * | 11/2004 | Taira et al. | 345/6 |
| 2004/0247174 | A1 | 12/2004 | Lyons | |
| 2005/0020910 | A1 * | 1/2005 | Quadling et al. | 600/424 |
| 2005/0070782 | A1 * | 3/2005 | Brodkin | 600/407 |
| 2005/0089822 | A1 * | 4/2005 | Geng | 433/215 |
| 2005/0131924 | A1 * | 6/2005 | Jones | 707/100 |
| 2005/0185711 | A1 | 8/2005 | Pfister | |
| 2005/0212910 | A1 * | 9/2005 | Singhal | 348/36 |
| 2006/0020363 | A1 * | 1/2006 | Orth et al. | 700/187 |
| 2006/0078842 | A1 * | 4/2006 | Sachdeva et al. | 433/24 |
| 2006/0154198 | A1 * | 7/2006 | Durbin et al. | 433/29 |
| 2006/0238617 | A1 | 10/2006 | Tamir | |
| 2006/0271229 | A1 * | 11/2006 | Kopelman et al. | 700/118 |
| 2006/0281971 | A1 | 12/2006 | Sauer | |
| 2006/0286501 | A1 * | 12/2006 | Chishti et al. | 433/24 |
| 2007/0030342 | A1 | 2/2007 | Wilburn | |
| 2007/0098237 | A1 * | 5/2007 | Yoo et al. | 382/128 |
| 2007/0103460 | A1 | 5/2007 | Zhang | |
| 2007/0146234 | A1 * | 6/2007 | Taira et al. | 345/6 |
| 2007/0183572 | A1 * | 8/2007 | Drummond et al. | 378/98.8 |
| 2007/0211081 | A1 * | 9/2007 | Quadling et al. | 345/632 |
| 2008/0013943 | A1 | 1/2008 | Rohaly | |
| 2008/0015727 | A1 * | 1/2008 | Dunne et al. | 700/118 |
| 2008/0070181 | A1 * | 3/2008 | Abolfathi et al. | 433/6 |
| 2012/0015316 | A1 * | 1/2012 | Sachdeva et al. | 433/24 |
| 2012/0290118 | A1 * | 11/2012 | Kaigler, Sr. | 700/119 |
| 2013/0003997 | A1 * | 1/2013 | Kassayan et al. | 381/151 |

* cited by examiner

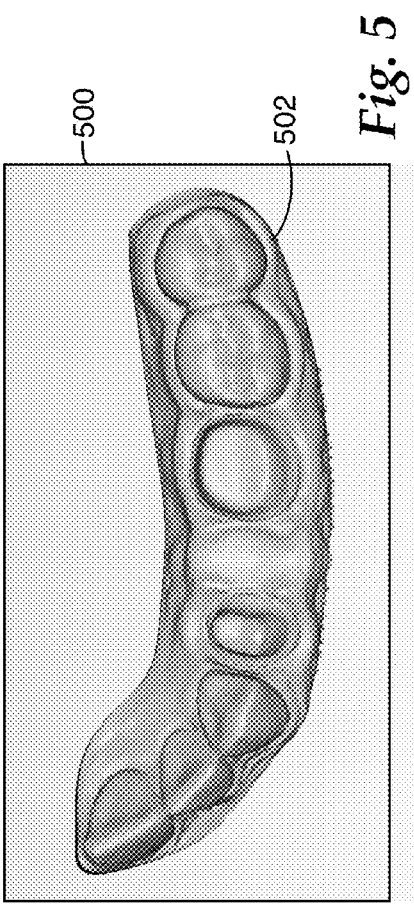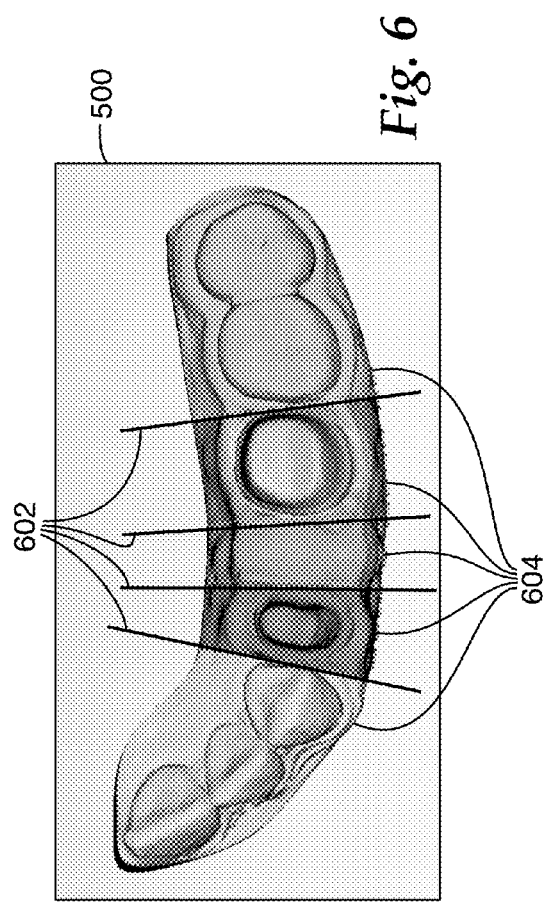

SYNCHRONIZED VIEWS OF VIDEO DATA AND THREE-DIMENSIONAL MODEL DATA

CROSS-REFERENCE TO RELATED APPLICATION

This application is a continuation of U.S. application Ser. No. 12/666,464, filed Nov. 15, 2010, which is a 371 National Stage of PCT/US2008/068522, filed Jun. 27, 2008, which claims the benefit of U.S. Provisional Patent Application Ser. No. 60/947,009, filed Jun. 29, 2007.

BACKGROUND

1. Field of the Invention

This disclosure relates to dentistry, and more particularly to tools and techniques for marking margins on three-dimensional digital models of dentition.

2. Description of the Related Art

Recent advances in dental technology have made it possible to capture highly accurate digital dental impressions. Current scanning techniques conceptually provide sufficient resolution to directly prepare physical models for a variety of dental restorations such as bridges, crowns, and the like, as well as dental appliances, dental prostheses, and so forth. However, intra-oral scanning presents numerous physical obstacles to obtaining accurate three-dimensional data around important areas such as the margin of a prepared tooth surface. This includes collapse of the tissue wall around the prepared tooth, as well as blood, saliva, and the like that may accumulate and obscure portions of the margin. In such situations, ambiguities in the resulting three-dimensional scan cannot be readily identified or resolved based solely upon the resulting three-dimensional model.

A need exists for improved techniques to process digital dental models. For example, a need exists for improved margin marking tools to assist with digitally preparing dental restorations.

SUMMARY

A digital production process for dental restorations is improved by supplementing views of three-dimensional models with still images of the modeled subject matter. Video data acquired during a scan of the model provides a source of still images that can be displayed alongside a rendered three-dimensional model, and the two views (model and still image) may be synchronized to provide a common perspective of the model's subject matter. This approach provides useful visual information for disambiguating surface features of the model during processing steps such as marking a margin of a prepared tooth surface for a restoration. Interactive modeling tools may be similarly enhanced. For example, tools for margin marking may synchronize display of margin lines between the still image and the model so that a user can interact with either or both of the visual representations.

In one aspect, a method disclosed herein includes creating a three-dimensional model from a sequence of image sets, each image set including a plurality of images of a subject, each one of the plurality of images captured from a different optical axis, the plurality of images including at least one video image; selecting a video image from the sequence of image sets, the video image containing a view of the subject from a perspective; displaying the video image in a user interface; and rendering the three-dimensional model in the user interface from the perspective.

The method may include selecting a different video image from the sequence of image sets, the different video image containing a second view of the subject from a second perspective; and rendering the three-dimensional model from the second perspective. Selecting a different video image may include receiving a user selection of one of a plurality of thumbnail images. Selecting a different video image may include receiving a user input from a video timeline control. The perspective may include a three-dimensional viewpoint relative to the subject. The perspective may include a distance from the subject. Creating the three-dimensional model may include capturing a plurality of image sets with a multi-aperture video camera. Creating the three-dimensional model may include capturing the video image from a center channel of the multi-aperture video camera.

A computer program product disclosed herein includes computer executable code embodied on a computer readable medium that, when executing on one or more computer devices, performs the steps of: creating a three-dimensional model from a sequence of image sets, each image set including a plurality of images of a subject, each one of the plurality of images captured from a different optical axis, the plurality of images including at least one video image; selecting a video image from the sequence of image sets, the video image containing a view of the subject from a perspective; displaying the video image in a user interface; and rendering the three-dimensional model in the user interface from the perspective.

The computer program product may include computer executable code that performs the steps of: selecting a different video image from the sequence of image sets, the different video image containing a second view of the subject from a second perspective; and rendering the three-dimensional model from the second perspective. Selecting a different video image may include receiving a user selection of one of a plurality of thumbnail images. Selecting a different video image may include receiving a user input from a video timeline control. The perspective may include a three-dimensional viewpoint relative to the subject. The perspective may include a distance from the subject. Creating the three-dimensional model may include capturing a plurality of image sets with a multi-aperture video camera. Creating the three-dimensional model may include computer executable code that may perform the step of capturing the video image from a center channel of the multi-aperture video camera.

A system disclosed herein includes a creating means for creating a three-dimensional model from a sequence of image sets, each image set including a plurality of images of a subject, each one of the plurality of images captured from a different optical axis, the plurality of images including at least one video image; a selecting means for selecting a video image from the sequence of image sets, the video image containing a view of the subject from a perspective; a displaying means for displaying the video image in a user interface; and a rendering means for rendering the three-dimensional model in the user interface from the perspective.

The system may include a second selecting means for selecting a different video image from the sequence of image sets, the different video image containing a second view of the subject from a second perspective, wherein the rendering means renders the three-dimensional model from the second perspective. Selecting a different video image may include receiving a user selection of one of a plurality of thumbnail images. Selecting a different video image may include receiving a user input from a video timeline control. The perspective may include a three-dimensional viewpoint relative to the subject. The perspective may include a distance from the subject. Creating the three-dimensional model may include capturing a plurality of image sets with a multi-aperture video camera. Capturing a plurality of image sets may include capturing the video image from a center channel of the multi-aperture video camera.

In another aspect, a method disclosed herein includes creating a three-dimensional model from a sequence of image sets, each image set including a plurality of images of a subject, each one of the plurality of images captured from a different optical axis, the plurality of images including at least one video image; rendering the three-dimensional model in a user interface from a perspective; selecting a video image from the sequence of image sets that contains a view of the subject most closely corresponding to the perspective; and displaying the video image in the user interface.

The subject may include dentition, the method including providing a tool for marking a margin of the dentition. The method may include receiving a user selection of a new perspective on the three-dimensional model and selecting a different video image from the sequence of image sets, the different video image containing a second view of the subject from a second perspective; and rendering the three-dimensional model from the new perspective. The method may include providing one or more of a zoom control, a pan control, and a rotate control to receive the user selection. The perspective may include a three-dimensional viewpoint relative to the subject. The perspective may include a distance from the subject. Creating a three-dimensional model may include capturing a plurality of image sets with a multi-aperture video camera. Capturing a plurality of image sets may include capturing the video image from a center channel of the multi-aperture video camera. The method may include selecting a plurality of video images from the sequence of image sets and synthesizing a composite video image that combines data from the plurality of video images to obtain the view of the subject. The composite video image may have a resolution higher than a resolution of any one of the plurality of video images.

A computer program product disclosed herein includes computer executable code embodied on a computer readable medium that, when executing on one or more computer devices, performs the steps of: creating a three-dimensional model from a sequence of image sets, each image set including a plurality of images of a subject, each one of the plurality of images captured from a different optical axis, the plurality of images including at least one video image; rendering the three-dimensional model in a user interface from a perspective; selecting a video image from the sequence of image sets that contains a view of the subject most closely corresponding to the perspective; and displaying the video image in the user interface.

The subject may include dentition, the computer program product including providing a tool for marking a margin of the dentition. The computer program product may include computer executable code that performs the steps of: receiving a user selection of a new perspective on the three-dimensional model; selecting a different video image from the sequence of image sets, the different video image containing a second view of the subject from a second perspective; and rendering the three-dimensional model from the new perspective.

The computer program may further include computer executable code that performs the step of providing one or more of a zoom control, a pan control, and a rotate control to receive the user selection. The perspective may include a three-dimensional viewpoint relative to the subject. The perspective may include a distance from the subject. Creating a three-dimensional model may include capturing a plurality of image sets with a multi-aperture video camera. Capturing a plurality of image sets may include capturing the video image from a center channel of the multi-aperture video camera. The computer program may include computer executable code that performs the step of selecting a plurality of video images from the sequence of image sets and synthesizing a composite video image that combines data from the plurality of video images to obtain the view of the subject. The composite video image may have a resolution higher than a resolution of any one of the plurality of video images.

A system disclosed herein includes creating means for creating a three-dimensional model from a sequence of image sets, each image set including a plurality of images of a subject, each one of the plurality of images captured from a different optical axis, the plurality of images including at least one video image; rendering means for rendering the three-dimensional model in a user interface from a perspective; selecting means for selecting a video image from the sequence of image sets that contains a view of the subject most closely corresponding to the perspective; and displaying means for displaying the video image in the user interface.

The subject may include dentition, the system including providing a tool for marking a margin of the dentition. The selecting means may include means for receiving a user selection of a new perspective on the three-dimensional model and selecting a different video image from the sequence of image sets, the different video image containing a second view of the subject from a second perspective; and rendering the three-dimensional model from the new perspective. The selecting means may include means for providing one or more of a zoom control, a pan control, and a rotate control to receive the user selection. The perspective may include a three-dimensional viewpoint relative to the subject. The perspective may include a distance from the subject. The creating means may include means for capturing a plurality of image sets with a multi-aperture video camera. The creating means may include means for capturing the video image from a center channel of the multi-aperture video camera. The system may include second selecting means for selecting a plurality of video images from the sequence of image sets and synthesizing a composite video image that combines data from the plurality of video images to obtain the view of the subject. The composite video image may have a resolution higher than a resolution of any one of the plurality of video images.

In another aspect, a method disclosed herein includes creating a three-dimensional model from a sequence of image sets, each image set including a plurality of images of a subject, each one of the plurality of images in each image set captured from a different optical axis; displaying one of the plurality of images in a first window; rendering the three-dimensional model in a second window; and synchronizing the first window and the second window to provide a common perspective on the subject.

The method may include receiving a user selection of a different one of the plurality of images and rotating the three-dimensional model to maintain the common perspective. The method may include receiving a user selection of a different one of the plurality of images and translating the three-dimensional model to maintain the common perspective. The method may include receiving a user selection of a different one of the plurality of images and scaling the three-dimensional model to maintain the common perspective. The method may include receiving a user selection of a different perspective of the three-dimensional model and selecting a new one of the plurality of images to maintain the common perspective. The method may include receiving a user selection of a different perspective of the three-dimensional model and creating a composite video image from two or more of the plurality of images to provide a common perspective on the subject.

A computer program product disclosed herein includes computer executable code that, when executing on one or more computing devices, performs the steps of: creating a three-dimensional model from a sequence of image sets, each image set including a plurality of images of a subject, each one of the plurality of images in each image set captured from a different optical axis; displaying one of the plurality of images in a first window; rendering the three-dimensional model in a second window; and synchronizing the first window and the second window to provide a common perspective on the subject.

The computer program product may include computer executable code that performs the step of receiving a user selection of a different one of the plurality of images and rotating the three-dimensional model to maintain the common perspective. The computer program product may include computer executable code that performs the step of receiving a user selection of a different one of the plurality of images and translating the three-dimensional model to maintain the common perspective. The computer program product may include computer executable code that performs the step of receiving a user selection of a different one of the plurality of images and scaling the three-dimensional model to maintain the common perspective. The computer program product may include computer executable code that performs the step of receiving a user selection of a different perspective of the three-dimensional model and selecting a new one of the plurality of images to maintain the common perspective. The computer program product may include computer executable code that performs the step of receiving a user selection of a different perspective of the three-dimensional model and creating a composite video image from two or more of the plurality of images to provide a common perspective on the subject.

A system disclosed herein includes creating means for creating a three-dimensional model from a sequence of image sets, each image set including a plurality of images of a subject, each one of the plurality of images in each image set captured from a different optical axis; displaying means for displaying one of the plurality of images in a first window; rendering means for rendering the three-dimensional model in a second window; and synchronizing means for synchronizing the first window and the second window to provide a common perspective on the subject.

The system may include control means for receiving a user selection of a different one of the plurality of images and rotating the three-dimensional model to maintain the common perspective. The system may further include control means for receiving a user selection of a different one of the plurality of images and translating the three-dimensional model to maintain the common perspective. The system may include control means for receiving a user selection of a different one of the plurality of images and scaling the three-dimensional model to maintain the common perspective. The system may include control means for receiving a user selection of a different perspective of the three-dimensional model and selecting a new one of the plurality of images to maintain the common perspective. The system may include control means for receiving a user selection of a different perspective of the three-dimensional model and creating a composite video image from two or more of the plurality of images to provide a common perspective on the subject.

In another aspect, a method disclosed herein includes displaying a three-dimensional model of dentition from a perspective; providing a plurality of video images of the dentition; selecting one of the plurality of video images that shows the dentition from the perspective; and displaying the one of the plurality of video images in a user interface with the three-dimensional model as an aid to visually determining a margin of the dentition.

The method may include displaying a margin on one or more of the three-dimensional model or the one of the plurality of video images. Displaying the margin may further include receiving a user modification of the margin and updating the display with a modified margin.

A system disclosed herein includes a display having a window for displaying a three-dimensional model of dentition from a perspective; a camera providing a plurality of video images of the dentition; selecting means for selecting one of the plurality of video images that shows the dentition from the perspective; and a second window in the display for displaying the one of the plurality of video images as an aid to visually determining a margin of the dentition.

The system may include margin display means for displaying a margin on one or more of the three-dimensional model or the one of the plurality of video images. The margin display means may include margin modification means for receiving a user modification of the margin and updating the display with a modified margin.

A computer program product disclosed herein includes computer executable code that, when executing on one or more computing devices, performs the steps of: displaying a three-dimensional model of dentition from a perspective; providing a plurality of video images of the dentition; selecting one of the plurality of video images that shows the dentition from the perspective; and displaying the one of the plurality of video images in a user interface with the three-dimensional model as an aid to visually determining a margin of the dentition.

The computer program product may include computer executable code that performs the step of displaying a margin on one or more of the three-dimensional model or the one of the plurality of video images. Displaying the margin may include computer executable code that performs the step of receiving a user modification of the margin and updating the display with a modified margin.

BRIEF DESCRIPTION OF THE FIGURES

The invention and the following detailed description of certain embodiments thereof may be understood by reference to the following figures.

FIG. 5 depicts a graphical die cutting operation.

FIG. 6 depicts a graphical die cutting operation.

DETAILED DESCRIPTION

Figure 1:
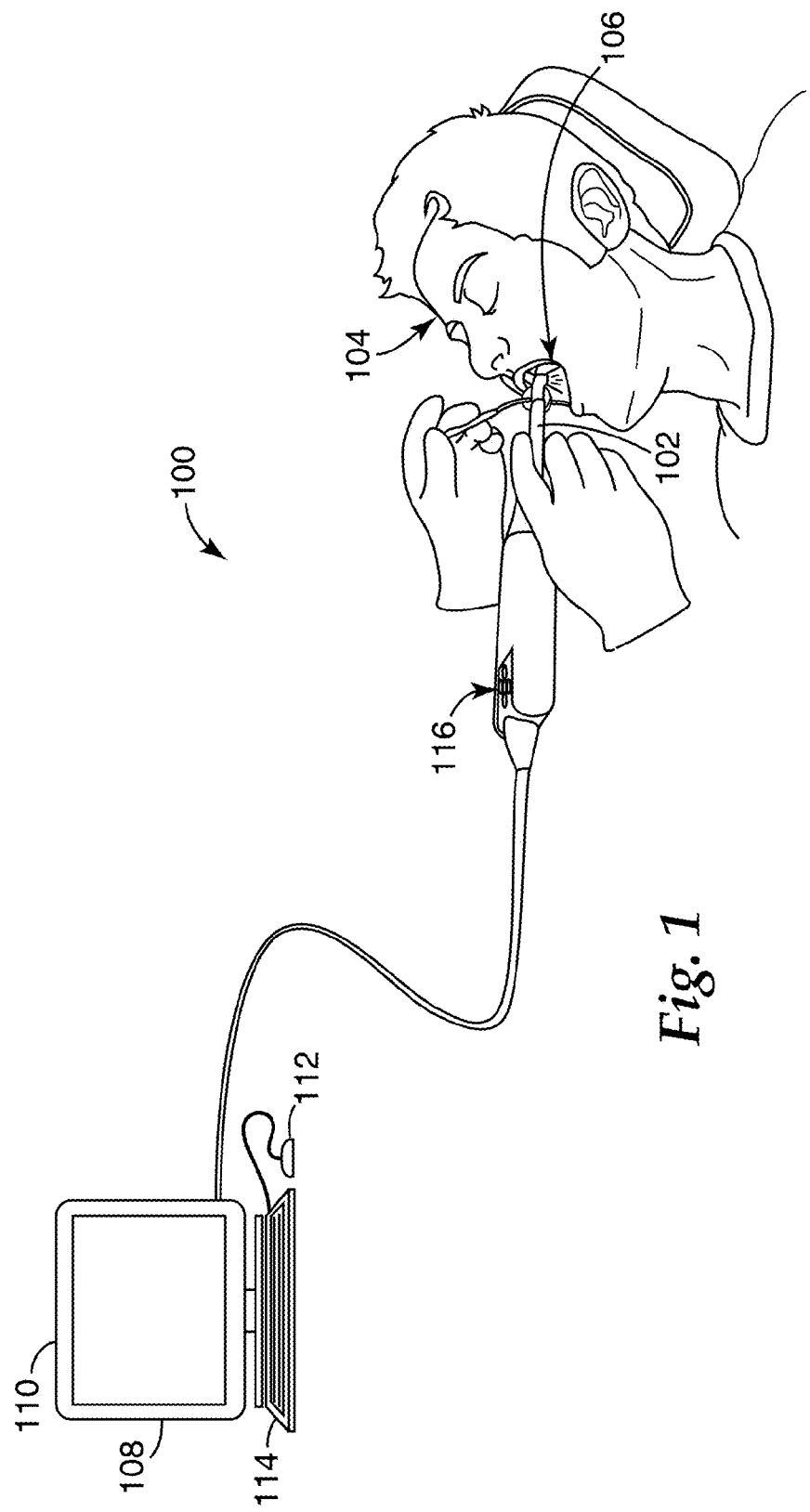
FIG. 1 shows a dental image capture system.

Described herein are systems and methods of addressing the identification, refinement, and other manipulation of margins for dental restorations based upon three-dimensional digital data captured from an intraoral scan. While the description emphasizes certain scanning technologies and certain techniques specific to marking margins on digital dental impressions obtained therefrom, it will be understood that additional variations, adaptations, and combinations of the methods and systems below will be apparent to one of ordinary skill in the art, such as fabrication of dental restorations not specifically described, or use of the following techniques outside a dental context. For example, the techniques described herein may be usefully employed to refine three-dimensional animation models acquired from scans of physical objects, or in a machine vision context to mark or evaluate scanned objects. All such variations, adaptations, and combinations are intended to fall within the scope of this disclosure. It will also be appreciated that the methods and systems described herein may be usefully employed for model verification and validation, as well as any other applications where useful comparisons between a video image and a corresponding three-dimensional model might be made.

In the following description, the term "image" generally refers to a two-dimensional set of pixels forming a two-dimensional view of a subject within an image plane. The term "image set" generally refers to a set of related two dimensional images that might be resolved into three-dimensional data. The term "point cloud" generally refers to a three-dimensional set of points forming a three-dimensional view of the subject reconstructed from a number of two-dimensional views. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional surface representation", "digital surface representation", "three-dimensional surface map", and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context.

A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that three-dimensional rendering technologies exist, and may be usefully employed with the systems and methods disclosed herein. For example, the system and methods described herein may usefully employ a holographic display, an autostereoscopic display, a display viewed with anaglyph glasses, a head-mounted stereo display, or any other two-dimensional and/or three-dimensional display. As such, rendering as described herein should be interpreted broadly unless a narrower meaning is explicitly provided or otherwise clear from the context.

The term "dental object", as used herein, is intended to refer broadly to subject matter specific to dentistry. This may include intraoral structures such as dentition, and more typically human dentition, such as individual teeth, quadrants, full arches, pairs of arches which may be separate or in occlusion of various types, soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

It will further be understood that terms such as "tool" or "control", when used to describe aspects of a user interface, are intended to refer generally to a variety of techniques that may be employed within a graphical user interface or other user interface to receive user input that stimulates or controls processing including without limitation drop-down lists, radio buttons, cursor and/or mouse actions (selections by point, selections by area, drag-and-drop operations, and so forth), check boxes, command lines, text input fields, messages and alerts, progress bars, and so forth. Thus in the following description the terms "tool", "control" and the like should be broadly construed unless a more specific meaning is otherwise provided or clear from the context.

FIG. 1 shows an image capture system. In general, the system 100 may include a scanner 102 that captures images from a surface 106 of a subject 104, such as a dental patient, and forwards the images to a computer 108, which may include a display 110 and one or more user input devices such as a mouse 112 or a keyboard 114. The scanner 102 may also include an input or output device 116 such as a control input (e.g., button, touchpad, thumbwheel, etc.) or a display (e.g., LCD or LED display) to provide status information.

The scanner 102 may include any camera or camera system suitable for capturing images from which a three-dimensional point cloud may be recovered. For example, the scanner 102 may employ a multi-aperture system as disclosed, for example, in U.S. patent application Ser. No. 11/530,413 to Rohály et al., the entire content of which is incorporated herein by reference. While Rohály discloses one multi-aperture system, it will be appreciated that any multi-aperture system suitable for reconstructing a three-dimensional point cloud from a number of two-dimensional images may similarly be employed. In one multi-aperture embodiment, the scanner 102 may include a plurality of apertures including a center aperture positioned along a center optical axis of a lens that provides a center channel for the scanner 102, along with any associated imaging hardware. In such embodiments, the center channel may provide a conventional video image of the scanned subject matter. In other embodiments, a separate video camera and/or channel may be provided to achieve the same result, i.e., a video of an object corresponding temporally to a scan of the object, preferably from the same perspective, or from a perspective having a fixed, known relationship to the perspective of the scanner 102. The scanner 102 may also, or instead, include a stereoscopic, triscopic or other multi-camera or other configuration in which a number of cameras or optical paths are maintained in fixed relation to one another to obtain two-dimensional images of an object from a number of slightly different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging, or any other technology suitable for acquiring three-dimensional data, or two-dimensional data that can be resolved into three-dimensional data. While the techniques described below can usefully employ video data acquired by a video-based three-dimensional scanning system, it will be understood that any other three-dimensional scanning system may be supplemented with a video acquisition system that captures suitable video data contemporaneously with, or otherwise synchronized with, the acquisition of three-dimensional data.

In one embodiment, the scanner 102 is a handheld, freely positionable probe having at least one user input device 116, such as a button, lever, dial, thumb wheel, switch, or the like, for user control of the image capture system 100 such as starting and stopping scans. In an embodiment, the scanner 102 may be shaped and sized for dental scanning More particularly, the scanner may be shaped and sized for intraoral scanning and data capture, such as by insertion into a mouth of an imaging subject and passing over an intraoral surface 106 at a suitable distance to acquire surface data from teeth, gums, and so forth. The scanner 102 may, through such a continuous acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthetic, to ensure proper fitting using a previous scan of corresponding dentition, such as a tooth surface prepared for the prosthetic.

Although not shown in FIG. 1, it will be appreciated that a number of supplemental lighting systems may be usefully employed during image capture. For example, environmental illumination may be enhanced with one or more spotlights illuminating the subject 104 to speed image acquisition and improve depth of field (or spatial resolution depth). The scanner 102 may also, or instead, include a strobe, flash, or other light source to supplement illumination of the subject 104 during image acquisition.

The subject 104 may be any object, collection of objects, portion of an object, or other subject matter. More particularly with respect to the dental techniques discussed herein, the object 104 may include human dentition captured intraorally from a dental patient's mouth. A scan may capture a three-dimensional representation of some or all of the dentition according to particular purpose of the scan. Thus the scan may capture a digital model of a tooth, a quadrant of teeth, or a full collection of teeth including two opposing arches, as well as soft tissue or any other relevant intraoral structures. The scan may capture multiple representations, such as a tooth surface before and after preparation for a restoration. As will be noted below, this data may be employed for subsequent modeling such as designing a restoration or determining a margin line for same. During the scan, a center channel of the scanner 102 or a separate video system may capture video of the dentition from the point of view of the scanner 102. In other embodiments where, for example, a completed fabrication is being virtually test fitted to a surface preparation, the scan may include a dental prosthesis such as an inlay, a crown, or any other dental prosthesis, dental hardware, dental appliance, or the like. The subject 104 may also, or instead, include a dental model, such as a plaster cast, wax-up, impression, or negative impression of a tooth, teeth, soft tissue, or some combination of these.

The computer 108 may be, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. In one current embodiment, the system can be operated to capture more than five thousand points per image set in real time using the techniques described herein, and store an aggregated point cloud of several million points. Of course, this point cloud may further processed to accommodate subsequent data handling, such as by decimating the point cloud data or generating a corresponding mesh of surface data. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the subject 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110. In another aspect, the display may include an autostereoscopic display capable of displaying stereo images.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom.

In an example of general operation of a three-dimensional image capture system 100, the scanner 102 may acquire two-dimensional image sets at a video rate while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system employs camera motion estimation to avoid the need for independent tracking of the position of the scanner 102. One useful example of such a technique is described in commonly-owned U.S. application Ser. No. 11/270,135, filed on Nov. 9, 2005, the entire content of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In some embodiments, the display may include a touch screen interface using, for example capacitive, resistive, or surface acoustic wave (also referred to as dispersive signal) touch screen technologies, or any other suitable technology for sensing physical interaction with the display 110.

Figure 2:
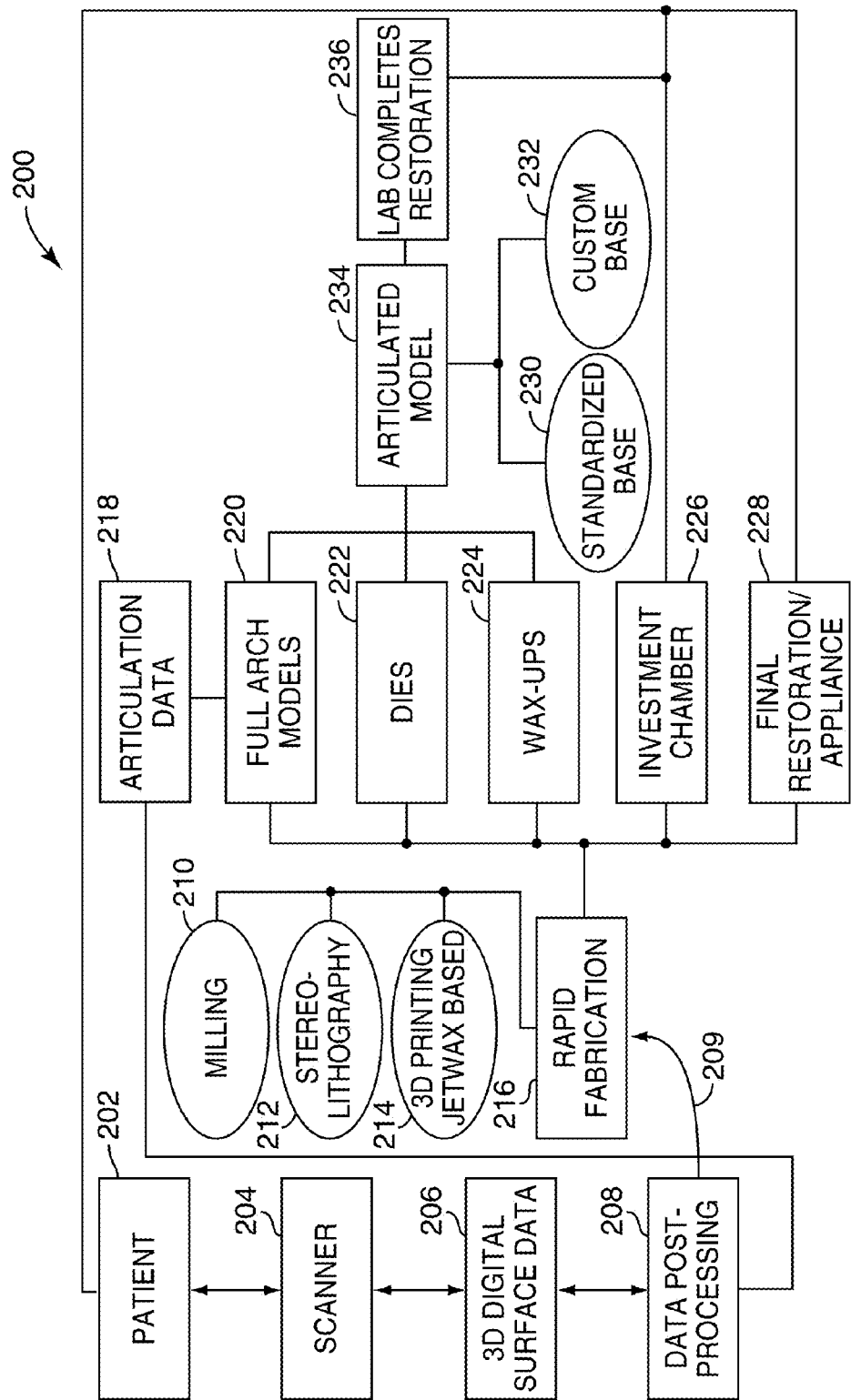
FIG. 2 is a block diagram of a generalized manufacturing process for dental objects.

FIG. 2 is a conceptual block diagram of participants in a generalized manufacturing process for dental objects. The system 200 may begin with a patient 202 being scanned by a scanner 204, such as the scanner 102 and image capture system 100 described above, to obtain a digital surface representation 206 of one or more intraoral structures. This may include scans before and/or after a surface has been prepared to receive a dental restoration or other dental object. So, for example, a pre-preparation scan may be taken to capture a shape of the original anatomy and any occlusion information useful in creating a restoration, and a prepared surface scan may be taken to use as a basis for creating the restoration, and in particular for shaping the restoration to the prepared surface. Articulation data relating to the orientation and/or relative motion of an upper and lower arch may also be obtained through one or more scans of the arches in occlusion, or through other techniques such as still images or video of the arches in various orientations, or various dimensional measurements captured directly from the arches, or a physical bite registration captured on a thin sheet of material.

The digital surface representation 206 may be processed with one or more post-processing steps 208. This may include a variety of data enhancement processes, quality control processes, visual inspection, conversion to a format suitable for rapid prototyping (or other manufacturing), and so forth. Post-processing steps may be performed at a remote post-processing center or other computer facility capable of post-processing the image file, which may be, for example a dental laboratory or a rapid fabrication facility. In some cases, this post-processing may be done by the image capture system 100 itself. Post-processing may involve any number of clean-up steps, including the filling of holes, removing of outliers, etc.

Data enhancement may include, for example, smoothing, truncation, extrapolation, interpolation, filling (e.g. surface to volume) and any other suitable processes for improving the quality of the digital surface representation 206 or improving its suitability for an intended purpose. In addition, spatial resolution may be enhanced using various post-processing techniques. Other enhancements may include modifications to the data, such as forming the digital surface representation 206 into a closed surface by virtually providing a base for each arch, or otherwise preparing the digital surface representation for subsequent fabrication steps.

In a quality control process, the digital surface representation 206 may be analyzed for the presence of holes or regions of incomplete or inadequate scan data. The digital surface representation 206 may also be automatically examined for unexpected curvature or asymmetry to a scanned arch, or other apparent defects in the acquired data. Other quality control processes may incorporate additional data. For example, a current scan may be compared to previous scans for the same patient. As another example, a selection of a dental restoration may be analyzed along with a scan of a tooth surface prepared for the restoration in order to evaluate the suitability of the surface preparation and any surrounding dentition for receiving the restoration. More generally, any process for evaluating data in the digital surface representation 206 with respect to its quality, internal consistency, or intended use, may be used in a post-processing quality control process.

The digital surface representation 206 may also be displayed for human inspection, such as by providing a perspective rendering of a point cloud or mesh of acquired surface data on a display. For example, a dentist or other individual acquiring a scan may select a portion of a dental model such as an arch, or particular teeth, for use in subsequent processing steps. A manual selection of portions of a model and/or scan may significantly reduce the amount of data required for a particular treatment. In addition, a manual identification of either model sections or video data may be followed by automated filtering of data. For example, once a dentist selects a particular tooth for subsequent processing, video data that is not associated with that tooth or one or more neighboring teeth may be excluded from further processing, and may, for example, not be transmitted to downstream processes such as the margin marking systems described below. At this time, or at other times in the post-scan processing, a user may review the digital surface representation 206 to mark a margin for a restoration. Details of this specific process will be described below in greater detail.

Following any manual or automated post-processing, the resulting digital model may be transmitted to a rapid fabrication facility 216, as indicated by an arrow 209. In addition, articulation data 218 in any suitable form may be transmitted for use in subsequent processing steps, as well as a prescription or other specification for manufacture of a restoration, appliance, hardware, and the like. The rapid fabrication facility 216 may be a dental laboratory, an in-house dental laboratory at a dentist's office, or any other facility with machinery to fabricate physical models from digital models. The rapid fabrication facility 216 may, for example, include a milling system 210, a stereo lithography system 212, or a three-dimensional printer 214, or some combination of these. The milling system 210 may include, for example, a CNC milling machine. Milling systems may be used to take a block of material and create a variety of outputs, including full-arch models, dies, wax-ups, investment chambers or a final restoration or appliance. Such blocks may include ceramic-based, particle-board, wax, metals or a variety of other materials.

Dental milling systems such as Procera from Nobel Biocare Inc., or Cerec from Sirona Inc. may also be used to create a final dental hardware component. The stereo lithography system 212 may include, for example, a Viper System by 3D Systems, Inc. The three-dimensional printer 214 may include, for example, an InVision HR printer from 3D Systems. Each of these fabrication techniques will be described in greater detail below.

The rapid fabrication facility 216 may use the articulation data 218 and the digital model to generate one or more dental objects, such as one or more full arch models 220, one or more dies 222, one or more waxups 224, one or more investment chambers 226, and/or one or more final restorations or appliances 228. Some components, such as the dies 222 and arches 220, may be inserted into an articulated model 234 such as an articulator with a standard base 230 or a custom base 232. A dental laboratory may employ these various components to complete a restoration 236, which may be returned to a dentist for placement into/onto the dentition of the dental patient.

A number of suitable rapid fabrication facilities are known in the art and may be usefully employed with the systems and methods described herein. A number of such techniques are described below by way of illustration and not limitation.

One suitable technique is milling. Milling is generally a subtractive technology in that material is subtracted from a block rather than added. Thus pre-cut workpieces approximating commonly milled shapes may advantageously be employed to reduce the amount of material that must be removed during a milling job, which may reduce material costs and/or save time in a milling process. Computerized Numerically Controlled ("CNC") milling is one suitable technique. Another useful milling technique for the dental fabrication processes is a copy milling system that permits manual or automated transfer of a three-dimensional form from a physical object to a milled target. CNC milling and other milling technologies can be employed for manufacturing dental models, dental model components, wax-ups, investment chambers, and other dental objects. In addition specialty dental milling equipment exists, such as the Cerec system from Sirona Dental. All milling systems that may be adapted to use in the dental applications described herein are intended to fall within the scope of rapid fabrication facilities as described herein.

Another suitable technique is stereo lithography using a stereo lithography apparatus ("SLA"). In general, an SLA employs a laser to sequentially cure layers of a polymer, typically a photocurable liquid resin, with a pattern that defines a three-dimensional object. One useful commercial embodiment of an SLA is the SCS-1000HD available from Sony Corporation. Stereo lithography is well-suited for the high volume production of dental models and dies, because parts may be batched on machines for rapid production. When optimized, these parts may be used in lieu of plaster dental models and other dental objects. A similar technology employs digital light processing ("DLP") to concurrently cure planar cross-sections of a polymer, and may also be usefully employed with the systems described herein.

Another suitable technique is three-dimensional printing. In general, a three-dimensional printer employs a print head to apply material such as curable photopolymers or powders in a layer-by-layer additive process. Three-dimensional printers are well suited to rapid fabrication of small parts such as wax patterns or wax-ups, as well as dies and other relatively small dental objects. One commercial system suitable for three-dimensional dental printing applications is the InVision HR printer from 3D Systems.

It will be appreciated that other rapid prototyping systems are known in the art. Thus, the terms fabricate, fabricating, and fabrication, as used herein, will be understood to refer to the fabrication technologies above, as well as any other rapid prototyping or other manufacturing technology that might be adapted to manufacture of custom dental objects, including, without limitation, selective laser sintering ("SLS"), fused deposition modeling ("FDM"), laminated object manufacturing ("LOM"), and so forth. Similarly, any of the above technologies, either alone or in combination, may operate as a means for fabricating, printing, manufacturing, or otherwise creating the dental objects described herein. It will be appreciated that the fabrication steps described above with reference to particular technologies may be followed by additional steps such as curing, cleaning, and so forth to provide a final product. The manufacturing techniques described above may be combined in various ways to provide a multimodal fabrication process. Thus, for example, a CNC milling machine may be used to create a die for a tooth requiring greater detail than an SLA can provide, while the SLA may be employed for a model of a dental arch that contains the die. This multimodal approach may deploy the advantages of various technologies in different aspects of the fabrication process, such as using stereo lithography for speed, milling for accuracy, and three-dimensional printing for high-speed fabrication of small parts.

Figure 3:
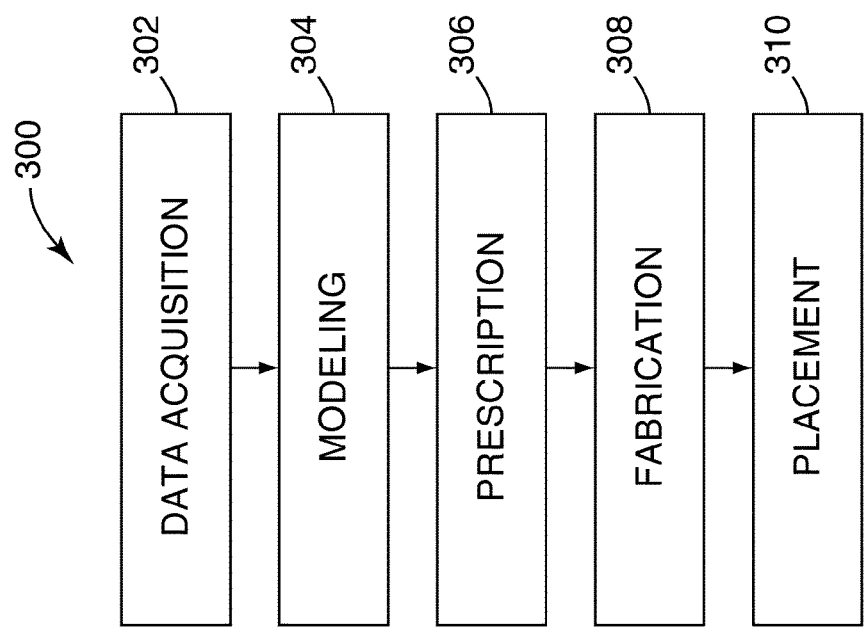
FIG. 3 is a high-level flow chart of a dental object fabrication process.

FIG. 3 is a high-level flow chart of a dental object fabrication process. This process 300 employs a three-dimensional representation of dentition acquired directly from an intraoral scan, and may advantageously bypasses a number of processing steps used in conventional dentistry.

In general the process 300 may begin with data acquisition, as shown in step 302. Data acquisition may include any acquisition of a digital surface representation, or other three-dimensional or other representation of dentition suitable for use in a dental object fabrication process. The data acquisition may be performed using, for example, the scanner 102 and image capture system described above with reference to FIG. 1. In certain embodiment, a number of different scans may be acquired, such as scans to establish articulation and occlusion of arches, or scans before and after a surface preparation, which may be used jointly to create a prosthetic or the like. In certain embodiments scans may be obtained at different resolutions, such as a relatively low-resolution scan for an opposing arch and a relatively high-resolution scan for the margin of a prepared tooth surface.

It will be understood that while the following description generally relates to operations performed outside a dentist's office, such as at a central processing location or a dental lab where margins are marked onto digital models, the user interfaces, tools, and techniques described herein may be usefully employed in a number of ways at the time of a scan, or before transmitting the scan data to a remote processing center.

For example, a dentist may employ the video review tools, either alone or in combination with synchronized views of a digital model, to qualitatively assess the suitability of a particular scan. Stereoscopic rendering of either the video image(s) and/or digital model may provide useful insights that the clinician can apply to determine whether a supplemental scan or an entirely new scan are appropriate.

In other embodiments, a dentist may perform some or all of the margin marking before transmitting data to a dental laboratory or other remote site.

In other embodiments, a dentist may tag frames of video data or points on a model surface with information that can be transmitted with the scan data to a remote site. This capability may be embodied in a tool for annotations provided within a graphical user interface such as the user interface described below. The annotations may include, for example, a prescription, margin information, margin marking instructions, or any other information relevant to margin marking or other steps in the dental restoration process. The information may be entered by selecting a point on a video image or digital model surface and entering any desired text, attachments, or other data or information. These annotations may be visually displayed as flags or other visual landmarks. In one aspect, the annotations may be provided on the video image. In another aspect, the annotations may be provided on the model. In another aspect, the annotations may be provided in one view, and displayed on both views.

It will be understood that other information, such as a camera model, distortion model, calibration data, and the like may be usefully transmitted along with or as a part of the prescription data for a particular patient and/or restoration. In addition, information such as header information inserted into frames of video data by a scanner may be transmitted. This header information, which may include details on a particular scanner (e.g., a serial number), lighting conditions for a scan, the region of dentition scanned, and so forth, may also be usefully transmitted, and may be employed for a variety of downstream uses such as automated determination of video metadata such as a view (e.g., buccal, lingual, distal, medial, occlusal, etc.) or an identification of teeth within a current image. By way of example and not limitation, this information may be employed to label thumbnail views used in the navigation techniques described below. In other embodiments, the camera model (camera parameters, calibration data, distortion data, and the like) may be stored at a remote location, with the selection of a camera model for a particular scan based on the identification of the scanner in the video metadata. This approach advantageously reduces the amount of data that must be transmitted with each scan, while providing full information to characterize the relationship between video data and a three-dimensional model at a remote location where the model is being viewed and/or manipulated.

In addition to supplementing model information as described above, a dentist or other scan creator may prepare a more compact data transmission by removing unneeded material from the video and/or model data. In general, this selection process applies the general principle that the video data required for a three-dimensional model reconstruction may be different (and typically greater) than the video data required for human video-assisted review of the model or modeling operations such as margin marking. For example, after identifying a specific tooth or teeth for a restoration or the like, the operator may delete unneeded video frames or model data, or may initiate an automated removal of unneeded data based upon the identification of what video data is relevant to the region(s) of interest. Regions of interest may include a prepared tooth surface, one or more adjacent teeth, one or more opposing teeth, a number of prepared teeth (such as for a bridge), and so forth. Video images and/or a corresponding model may be stereoscopically rendered within a user interface at the site of the scan to assist with this pre-transmission selection of regions of interest. The user interface may incorporate some or all of the features described below with respect to a user interface for margin marking. In general, a number of criteria may be employed for selecting regions of interest or relevant image frames for a dental procedure such as margin marking. For example, frames of video data may be selected for coverage of the image data, such as complete coverage of the regions of interest or optimal (e.g., non-overlapping or overlapping a predetermined amount) coverage of the regions of interest.

Similarly, frames may be selected based upon orientation of the image data such as the best viewing angle, either for visual inspection or accuracy of calculated three-dimensional data (or both). Selection based upon orientation may further include selection of multiple frames with substantially different perspectives on each surface point or surface area in order to ensure or improve the chances of a number of unique perspectives on each surface feature. It will also be appreciated that, even within a region of interest, the video image capture rate of the scanner may be such that only a small number of video images are required for meaningful human review. Thus for example, a data reduction process may automatically eliminate every other frame, four out of five frames, nine out of ten frames, or any other number of frames selected to preserve adequate video data for video-assisted review as described herein. In a manual technique, a user may explicitly select the relevant video images. In an semi-automatic technique, a user may graphically identify points or regions of interest and the video data may be processed to select video images satisfying one or more selection criteria such as those described above. In a fully automated procedure, a user may simply identify the relevant teeth or provide a prescription, and a computer program may process the video images to determine regions of interest and select frames of video data accordingly.

Thus in one aspect there is disclosed herein a technique for reducing the size of a digital dental model by removing video frames and/or model data that are not relevant to a restoration. In another aspect, there is disclosed herein a technique for reducing the size of a digital dental model by removing video frames and/or model data that are not required for marking a margin. In addition to detailed video and or model data for the selected regions, a lower quality model of additional dentition may be transmitted with the selected regions, such as a low quality full arch model for use in a physical or virtual dental articulator. In another aspect, a similar subset of video images may be selected when displaying thumbnail views in a user interface as described below. Thus images of significance in a dental restoration procedure such as margin marking may be selected for display in a video navigation user interface such as the interface described below. These images may be further labeled with orientation information for a user such as a view (buccal, lingual, distal, mesial, etc.), which may be displayed textually or through an illustrative icon, diagram, three-dimensional compass, or any other suitable visualization technique.

Once suitable data has been acquired, one or more modeling operations may be performed, as shown in step 304. This may include modeling steps such as ditching a virtual die of a digital dental model, specifying a tooth for treatment, filling holes or otherwise correcting data, bite registration, and/or fully designing a restoration, prosthetic, hardware or other dental object(s), as well as any other modeling or digital model manipulation useful in a dental context. Modeling may be performed using a variety of commercially available Computer Automated Design ("CAD") or other three-dimensional modeling tools, as well as tools incorporating the additional features described below in greater detail.

For example, modeling may include bounding the surface representation to form a solid, and then creating a void space, or collection of void spaces within the solid that do not affect dentally significant surfaces such as the dentition or surrounding soft tissue. This may advantageously result in significant reductions in material required to fabricate a dental model from the voided digital model, thus reducing material costs as well as time to manufacture dental models. Modeling may also include creating or manipulating a margin on a prepared tooth surface. A number of other modeling steps are described with reference to specific fabrication processes below. It will be appreciated that the term "modeling" as used herein may refer to any processing of a digital dental model including fully automated, semi-automated, and/or manual processes such as those noted throughout this description.

As shown in step 306, a prescription may be prepared. This specifies a type of restoration, prosthetic, or the like, and may include a variety of additional information related to a manufacturer, color, finish, die spacing, and so forth. It will be appreciated that the prescription step 306 may be performed before the modeling step 304, such as in a process where a dentist transmits the initial digital surface representation from a patient to a dental laboratory along with a prescription, leaving some or all of the modeling to the dental laboratory.

As shown in step 308, one or more dental objects may be fabricated. Fabrication may be performed using any of the fabrication technologies described above, either alone or in various combinations, using data from one of the modeling systems described above, which may be reformatted or otherwise adapted as necessary for a particular printing, milling, or other fabrication technology. Also, as will be clear from some of the examples below, fabrication may include a combination of different fabrication technologies. For example, dental model may be three-dimensionally printed with a space for a die, and the die may be milled of a different material for use in subsequent processing steps. Thus, the term "fabrication" as used herein is intended to refer to any suitable fabrication technology unless a specific fabrication technology is explicitly identified, or otherwise clear from the context. A number of specific fabrication examples are discussed below in greater detail.

As shown in step 310, a prosthetic or other dental object may be returned to a dentist for placement into a patient's dentition.

It will be appreciated that the above processes, as well as the methods and systems described below, may be realized in hardware, software, or any combination of these suitable for the data acquisition, modeling, and fabrication technologies described herein. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer and/or fabrication facility and/or dental laboratory in a number of ways or all of the functionality may be integrated into a dedicated, standalone device. All such permutations and combinations are intended to fall within the scope of the present disclosure.

It will also be appreciated that means for performing the steps associated with the processes described above may include any suitable components of the image capture system 100 described above with reference to FIG. 1, along with any software and/or hardware suitable for controlling operation of same. All such realizations and means for performing the processes disclosed herein are intended to fall within the scope of this disclosure.

Figure 4:
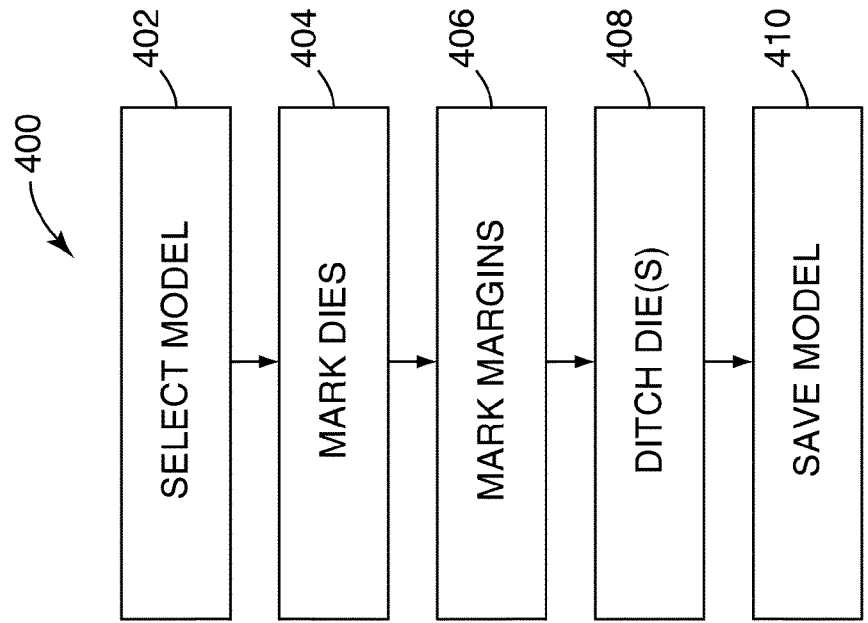
FIG. 4 shows a generalized process for working with digital dental models using the tools described herein.

FIG. 4 shows a generalized process for working with digital dental models using the tools described herein, and more particularly for preparing a model for use in fabrication of a dental restoration such as a crown.

In a user interface, command line interface, or the like, a user such as a dental technician may select a model from a work queue of digital models, as shown in step 402. This may be, for example, a queue stored on a local system, or a queue stored at a remote location accessible through a web-based portal for dental laboratories or other dental professionals. It will be understood that while a queue generally includes any system for distributing modeling projects to one or more users on a systematic bases such as a file server, content management system, or the like, the digital dental models and accompanying data may also be represented simply as a file (or group of files) located in a local computer directory or a file (or group of files) received over a network. The model may include, for example, relevant scans such as a digital dental impression acquired before and after a dentist's preparation of a tooth surface for a restoration. Other information may also be usefully included, such as dental prescription information to guide the user and video data acquired during the scan(s) used to obtain the digital dental impression. This latter data may be used, for example, as an aid to margin marking as described in greater detail below.

After selection of a particular model, a user may mark dies within the model, as shown in step 404. In general, separation into dies permits easier handling of the operative tooth or teeth during subsequent physical (and digital) processing, and the individual dies will be manufactured as separate pieces for use in a dental laboratory. Cutting into dies may include presenting the model to a user along with tools for the user to control display (e.g., rotational orientation, zoom, pan, etc.) of the model and tools for the user to define one or more dies within the model. In one embodiment, a die cutting tool may permit the user to define vertical planes through a model at locations that separate teeth of an arch. An example of this operation is depicted in FIGS. 5-6 below.

After a model has been separated into dies, a user may mark margins for restorations as shown in step 406. A user may be prompted to identify one or more dies that require margin marking. Once one or more dies have been specified, a user interface may present a three-dimensional rendering of one of the specified dies, and may provide a graphical tool for marking points along an intended margin within the user interface. Again, the interface may include tools for controlling display of the model, such as rotational orientation, zoom, pan, and so forth, so that a user can conveniently navigate around the model during marking. A margin marking tool in the interface may permit selection of points along a surface of the model, and may form a margin line through any suitable algorithm for joining the points into a continuous, closed loop on the tooth surface. The tool may permit an addition of points, a deletion of points, and/or a movement of points. The tool may also permit selection and/or de-selection of points for group operations such as joining into a margin line, deleting, moving, and so forth. A number of useful interface features to assist with margin marking are described in greater detail below.

Once the margins have been marked, the dies may be ditched as shown in step 408. In general, this operation entails removal of portions of the die(s) below the margin line to permit easier identification of the margin line during subsequent handling steps. Ditching may be automated by processing the model to remove material below the margin line (or reshape the surface where a surface-only representation of the model is used). Manual ditching may also be supported through user interface tools that permit removal of model material. A combination of automated and manual techniques may also be employed.

Once the die has been cut, the margin has been marked, and the model has been ditched, the model may be saved for further processing as shown in step 410. The user may then return to the work queue to select another model as shown in step 402. More generally, the model and its various parts (e.g., the dies) may be stored at any stage of processing so that a user may save any current work and return to the saved project at a later time. While not specifically depicted, it will be appreciated that a user may select a new model from the work queue (step 402) before completing a previously selected model, so that the user can maintain any number of models at various stages of completion according to scheduling demands, personal preferences, or any other criteria.

It will be understood that the operations described above may be distributed among a number of locations involved in a digital dental workflow. For example, models may be originally created by a dentist using a digital scanner such as any of the scanners described above. The scanned model may be transmitted over a data network (along with prescription information and any other useful data) to a central repository that stores scan data and provides a secure interface for downstream users. Models may be selected from the repository in work queue fashion as described above by a dental technician at a dental lab or other facility, and the dental technician may cut and mark the models as appropriate. The technician may then apply any suitable ditching, or the cut and marked model may be returned to the central repository or some other post-processing location for automated ditching. Once returned to the central repository, the dies, prescription, and other data may be provided (again through a secure interface) to a rapid fabrication facility which may manufacture corresponding dental objects and forward them to a dental laboratory for finishing. While this is one example of a workflow that usefully distributes processing steps according to competence and capabilities, it will be understood that numerous other arrangements are possible, and may usefully be employed within the scope of the systems and methods described herein.

In one aspect, the methods described above may be employed to prepare models for rapid fabrication or the like, resulting in the fabrication of a physical model from a digital model of a die that has been cut, marked (on the margin), and ditched as generally described above. This in one aspect, a method described herein includes selecting a digital dental model; cutting at least one die from the digital dental model to provide a die model; marking a margin on the die model to provide a marked model; ditching the marked model to provide a ditched model; and fabricating a physical model from the ditched model. The method may include transmitting the ditched model to a remote data repository, to a dentist for review, or to a rapid fabrication facility for creation of the physical model.

FIGS. 5 and 6 depict a graphical die cutting operation that may be employed in a user interface for handling digital dental models. As shown in FIG. 5, a model 502 such as a scan of a dental arch may be graphically depicted in a user interface 500 by rendering the model 502 from a desired perspective. It will be understood that while a single arch is depicted, the model 502 may include multiple arches, including opposing arches, or may include a portion of an arch such as one or more teeth of interest. As shown in FIG. 6, a graphical tool may permit a user to specify one or more cuts 602 within the model 502 to segment the model into one or more sections 604, including one or more dies or individual teeth, also known as operative teeth (for a restoration such as a bridge, a die may include more than one tooth). Each section 604 may then be individually processed as appropriate. While the cuts 602 are depicted as lines through an appropriately oriented model, the graphical cutting tool may employ a number of different techniques for segmenting the model 502 including lines (which might define vertical planes), planes, or the like. Where planes are used to define sections 604 of the model 502, a tool may provide any suitable graphical representation of the planes within the user interface, and may permit a user to add, remove, or reposition the planes. The tool may also, where appropriate, permit a user to skew the planes off vertical to achieve a desired segmentation of the model 502. It will be understood that cutting a digital dental model into segments such as dies may be performed using a number of user interface tools, and may be digitally represented using a number of techniques. For example, the model may be separated into a number of separate surface models for each segment of the original model, or the cut planes used to define the segments may be associated with the original model to represent various sections thereof. Any techniques suitable for digitally representing the segmentation of the original model into a number of segments such as dies may be used with the systems and methods described herein.

Figure 7:
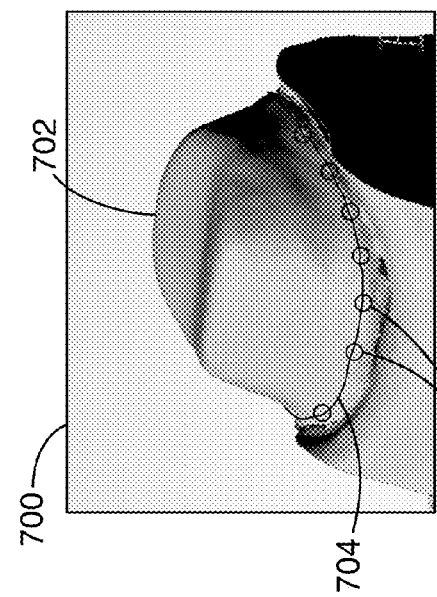
FIG. 7 depicts a graphical margin marking operation.

FIG. 7 depicts a graphical margin marking operation that may be employed in a user interface for handling digital dental models. As shown in FIG. 7, a model 702 such as a die from one of the digital dental models described above may be graphically depicted in a user interface 700 by rendering the model 702 from a desired perspective. A margin line 704 may be created within the model 702 by selecting one or more points 706 on a surface of the model 702 (where a restoration is to meet the prepared tooth surface) and joining the points 706 in a continuous closed loop of the margin 704. The user interface 700 may provide tools for controlling a perspective or point of view for rendering the model 702, such as for rotating, panning, zooming, and the like. In the following description, terms such as perspective and point of view are used interchangeably to refer to data describing a position and orientation from which a subject is being viewed. In three dimension space, this typically includes x, y, and z coordinates as well as rotational orientation on three axes. The user interface 700 may also provide tools for manipulating the points 706, such as for creating, deleting, or moving points, as well as for selecting and/or de-selecting points for group operations such as a move or delete. The tool(s) may include an undo feature for undoing one or more previous operations. The points 706 may be jointed automatically or manually, or some combination of these, such as through a tool in the interface 700 that automatically interconnects all points not joined manually, or a tool that suggests a next point based upon extrapolation or interpolation of existing points. The margin line 704 may be represented as a line, a set of line segments, a set of points, or any other suitable data set, which may be defined in a coordinate system of the model 702 (and by extension, in a coordinate system of the model of FIGS. 5 and 6, or any other digital model from which the operative tooth model was obtained). In general, while two-dimensional user interfaces are depicted in these drawings, the user interface 700 of the systems and methods described herein may employ any suitable two-dimensional or three-dimensional rendering techniques, including the various stereoscopic three-dimensional interfaces described herein.

Figure 8:
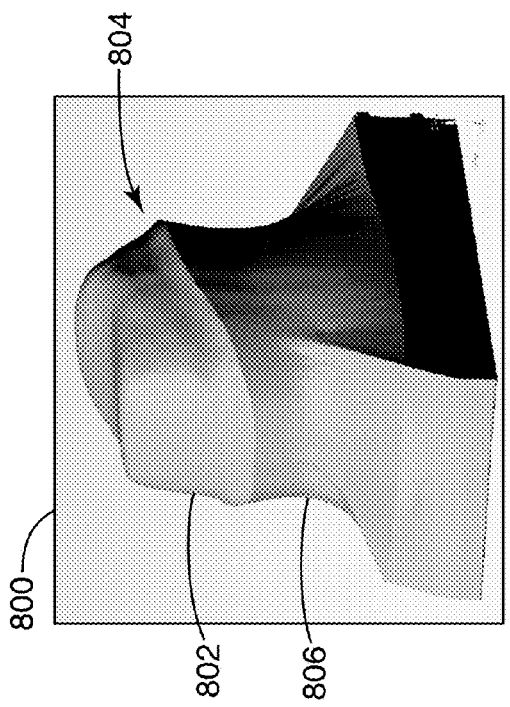
FIG. 8 depicts a graphical ditching operation.

FIG. 8 depicts a graphical ditching operation that may be employed in a user interface 800 for handling digital models. Once a margin line 802 has been defined for a die 804, ditching the die may be manually or automatically performed to provide a tooth base 806 for convenient handling of the resulting physical model used by a dental laboratory to create a restoration, and to make the margin line more readily visible in digital and physical models. With a properly specified margin line 802, ditching of the die is amenable to a high degree of automation. The user interface 800 may nonetheless provide tools for specifying various ditching parameters (depth, amount of material removal, etc.) and for inspecting the resulting ditched die. The user interface 800 may also provide tools for manually ditching, and/or for refining an automatically ditched die. Where highly detailed dental models are used, processes such as automated ditching may be advantageously performed at a digital data center such as the remote data repository described above.

Figure 9:
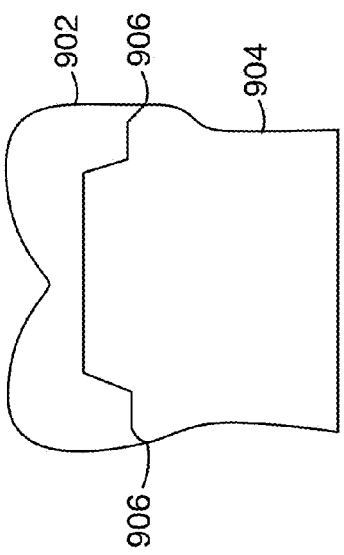
FIG. 9 illustrates an automated margin marking technique.

FIG. 9 illustrates an automated margin marking technique. One useful technique for automated margin marking employs a direct comparison of a tooth surface before and after preparation for a restoration. As depicted in FIG. 9 in a cross-sectional view, a model of a tooth surface before preparation for a restoration 902 may be registered with a model of a tooth surface after preparation for the restoration 904, where the pre-prep model 902 includes the volume of the post-prep model 904, as well as additional tooth structure. A line 906 formed on an exterior edge of the registered models (only two points on this line are visible in FIG. 9 at the left and right edges of the cross section) defines the margin line for the prepared tooth surface. The line 906 may be algorithmically identified using a Boolean XOR of the surfaces or volumes of the registered models, or using any of a number of other suitable edge finding techniques.

For example, contour evaluation may be applied to algorithmically identify the margin on the post-prep model 904 (or an associated pre-prep model) in three-dimensions. Similarly, edge finding techniques may be applied to still video images, with the results mapped to the three-dimensional model using, for example, the techniques described herein. In another embodiment, two-dimensional and three-dimensional techniques may be used in conjunction with results averaged or otherwise combined to derive a single margin line. In a semi-automated embodiment, image-based and model-based techniques may be separately applied, and a user may be permitted to select which result is used for a margin line, or the user may be permitted to select portions of the margin line from each result.

Figure 10:
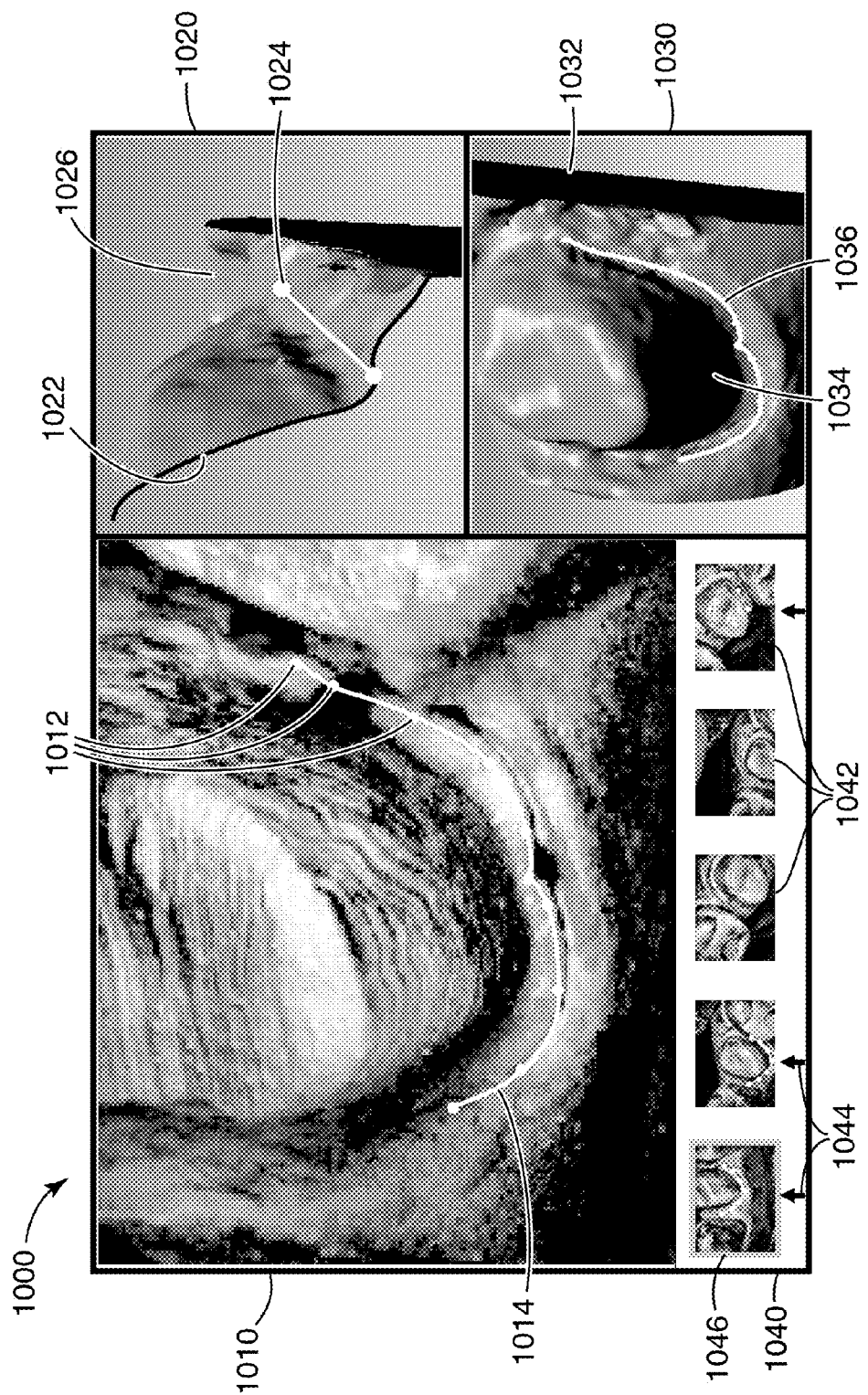
FIG. 10 shows a user interface for visually-assisted margin marking.

FIG. 10 shows a user interface for visually-assisted margin marking. A number of the processes described above are relatively straightforward and amenable to automated or computer-assisted modeling techniques. However, margin marking presents particular difficulties due to the likely presence of gross errors in a digital surface scan of dentition resulting from blood, saliva, or displaced soft tissue around the critical scan areas for a margin. The following interface addresses these difficulties by supplementing a display of a three-dimensional model with video images obtained during a scan. This interface is particularly suited to video-based scanning techniques such as a multi-aperture camera that includes a center channel for capturing video, as described generally above.

The user interface 1000 may include, for example, a video image window 1010, a cross-sectional view window 1020, a model view window 1030, and a video control window 1040.

One or more of these windows 1010-1040 may be stereoscopically rendered, or otherwise displayed in three-dimensions using available data such as the three-dimensional model, video image pairs, and/or sequences of images that can be warped to provide suitable stereo image pairs. The model view window 1030 and the cross-sectional view window 1020 employ two-dimensional rendering based upon a three-dimensional model, so stereoscopic rendering in these windows is a relatively straightforward application of known stereoscopic techniques. Where a multi-aperture or multi-camera image sequence is provided, the still image in the video image window 1010 may also be stereoscopically rendered based upon depth information encoded in stereo image pairs or the like. In one aspect, this stereoscopic image may be synthesized based upon a center channel image (where available), the reconstructed 3D model, and a camera model that provides mappings between image and object space. In one aspect, a user may switch between an originally acquired stereo image pair and the synthesized stereoscopic image to permit qualitative evaluation and/or validation of the three-dimensional digital model.

The video image window 1010 may display a still image from a video of a subject. The video may have been acquired during a three-dimensional scan, such as from a center channel of a multi-aperture camera, or from a video camera in a nearby, fixed, and known location relative to a scanning device. In general, a variety of handheld scanners are know that employ a variety of techniques for obtaining three-dimensional images including structured light or laser techniques, time-of-flight techniques, single-camera video techniques, multi-camera. multi-aperture, or split-pupil video techniques, and so forth. Although there are exceptions, these techniques largely rely on three-dimensional reconstruction algorithms that either require camera path data as an input or derive camera path data during processing of scan data. In other words, for each video image obtained during a scan, there is a substantially corresponding, known, concurrent camera position that includes camera position and rotational orientation relative to a subject being scanned. Thus for a still image displayed in the video image window 1010, a perspective or point of view of the scanner on the image content—in this case, the subject is a prepared tooth surface—can be determined. This information is useful for synchronizing views with the perspective view window, as will be described in greater detail below. Where non-video scanning techniques are employed, data may be supplemented with concurrent two-dimensional video that provides still images to supplement margin marking and other procedures as generally described herein.

Orientation information may be usefully displayed within (or otherwise in association with) the video image window 1010. For example, to assist a user with orientation of the image within the context of dentition, the video image window 1010 may display a viewpoint (e.g., buccal, lingual, distal, mesial, etc.) and/or distance of the current image, any of which may, as noted above, be determined from the scanner position data obtained during a scan. Further, a user control may be provided for direct selection of orientation. For example, a user may textually or graphically select an orientation for which a view of the current tooth or tooth surface is desired. The user interface may responsively select an image that contains an orientation of the subject matter that most closely corresponds to the selected orientation and display this image in the video image window 1010. In addition, the video control window 1040 described below may be responsively updated, such as be selecting a group of thumbnail images 1042 having a variety of different perspectives on the tooth surface selected, or a number of predetermined closely adjacent orientations.

In another aspect, a variety of image enhancement techniques may be applied to the working image(s) displayed in the video image window 1010 to enhance visual quality of the displayed image. For example, the display may employ locally adaptive contrast enhancement or contrast limited adaptive histogram equalization, or any other suitable techniques. The display may also, or instead, employ other information such as distance from a light source or information available from a corresponding three-dimensional model to control color, intensity, and the like for improved visual display of the still video image(s). Pseudo-coloring may also be employed advantageously, such as by shading an area around a margin or accenting areas of high spatial contrast. It will be understood that the image enhancement techniques described herein may be employed to assist margin marking or other dental operations as well as during or immediately after a scan as an aid to video review by the scan operator.

As described below, in one aspect the system operates to synchronize a viewpoint or perspective of a subject in the video image window 1010 and the model view window 1030. A number of techniques may be employed in order to maintain consistent visual information among the various windows of the user interface 1000. For example, the video image may be undistorted to more closely match depth information apparent in a stereoscopically rendered three-dimensional model. In one embodiment, the three-dimensional model accurately reflects the physical, three-dimensional counterpart and incorporates any calibration data, camera parameters, distortion models, and the like, so the preferred technique would be to undistort the video image accordingly for display. As a significant advantage, this approach permits a simple pinhole projection characterization of the mapping between the video image space and the digital model space, which can significantly reduce computation time for mappings between the two representations. However, it is possible and may be desirable in certain cases to distort the three-dimensional model to spatially correspond to the stereoscopically rendered video image. In either case, spatial correspondence may generally be achieved by mapping data across the camera model, calibration data, and the like used to create the three-dimensional model from the video data. This adjustment may include a distortion model for the camera system, which may account for x, y, and/or z dependent distortion in one or more channels of the camera system, as well as scene parameters such as viewing angle and the like.

Other techniques for conforming images in the various displays include adaptations of the still image display to a perspective selected in the model view, such as by texture mapping of video data onto the model, or warping, combining or otherwise processing existing image pairs to synthesize a perspective corresponding to the model view.

A number of points 1012, which may be user-positioned points or computer-positioned points, define some or all of a margin line 1014 (a partial margin line is illustrated by way of example and not limitation) within the video image window 1010. Points 1012 may be controlled with a user interface tool such as a cursor, along with any drop down menus, lists, scroll bars, keystrokes, or other controls suitable for adding, deleting, and moving points 1012. In addition, points 1012 may be selected or de-selected for group operations such as joining a group of points (to form some or all of a margin), moving a group of points, deleting a group of points, or adjusting a group of points to create a smoother margin line, or to algorithmically move points to more likely margin positions based upon curvature analysis, data concerning an unprepared tooth surface, or any other available information in combination with various techniques known in the art. Other more processing-intensive functions may also be provided, such as recommending a point location within a region around a current cursor position, completing the closed loop of a margin line based on one or more user-selected points, or looking for possible outliers in a current point set that defines a margin line. Where the video image window 1010 is stereoscopically rendered, a three-dimensional cursor may also be provided to accommodate user navigation within the rendered three-dimensional space. The three-dimensional cursor may be similarly employed in any of the windows 1010, 1020, 1030, 1040 that employ stereoscopic or other three-dimensional rendering techniques.

A number of useful features may be incorporated into a three-dimensional cursor. For example, the three-dimensional cursor may effectively behave as if it were attached to the surface of the imaged model (or stereoscopic video image) so that user motions (such as with a mouse) in a two-dimensional plane are projected onto the corresponding image locations relevant to the surface of the stereoscopically rendered image in the stereoscopic coordinate system. This technique works well with the systems described above where the video and model displays contain projections with unique surface locations for each screen location (such as a pixel or the like). However, in certain embodiments, additional three-dimensional functions may be provided that are not attached to the projected surface. This may include, for example, validation of the model and/or stereo images, editing the model based upon the stereo video images, and so forth. In such instances, an additional control such as a mouse scroll wheel may be employed to provide an additional degree of freedom for user input.

While three-dimensional input may permit unconstrained cursor movement within the stereoscopically rendered three-dimensional space, the third user input (e.g., scroll wheel) may also be further adapted for use with the margin marking operations described herein. For example, using the interface, tools, and three-dimensional cursor described herein, a user may directly edit the digital model in the model view window 1030, such as to create better agreement between video images and the three-dimensional model. There may be numerous reasons for such an edit. For example, with reference to the video, a user may identify artificial objects in a field of view such as cord, saliva, blood, and so forth. As another example, the video-based stereoscopic rendering and the model-based stereoscopic rendering may appear different. This may occur where, for example, the stereoscopic video is derived directly from image pairs obtained during a scan, while the model is derived using a camera model (e.g., camera parameters, calibration data, distortion data, and the like). A user may address these variations by selecting a point on the stereoscopically rendered surface of the model (or the video image) and moving the point freely in three dimensions. For example, the scroll wheel may control movement of the surface point in the z-axis of the screen, or in a direction normal to the surface. Further a user may control the extent to which surrounding points follow the movement. This technique may also be employed to sharpen the margin where the margin on the model appears overly rounded, or otherwise deviates from the margin depicted in the video image (or temporally adjacent images that provide clearer visual content). In one aspect, these tools permit direct manipulation of the digital model and/or stereoscopically rendered video image. In another aspect, these tools enable validation of the digital model by direct comparison to the source image data.

In either case, the user-provided model revisions may be used to revise the mapping of the model to the video image so that the user's changes are retained throughout any subsequent model operations. Another useful application is to segment individual teeth where the model appears to physically couple or bridge adjacent teeth across an interproximal gap.

The cross-sectional view window 1020 may be included within the user interface 1000 to assist a user in identifying contours of a tooth surface, and in particular for more accurate manual location of a margin. Cross-section view: this view shows the cross-section of the currently selected edit area point to help identify high curvature areas. The window 1020 may display one or more of a cross-section 1022 of a subject, such as at a current edit point 1024 (which may be any of the points 1012 displayed in the video image window 1010), or a perspective of the digital model 1026 beginning at a planar cross-section that includes the current edit point 1024, or some combination of these. The orientation of the planar cross-section through a subject may vary, although for purposes of discriminating contours, an orientation having the steepest or most varied slope may suitably be selected. A plane normal to the margin line may also be usefully employed. Points such as the current edit point 1024 or other points of the margin line, and changes thereto, may be synchronized with points displayed in the video image window 1010 and/or the model view window 103 as generally described above.

The model view window 1030 may be included within the user interface 1000 to provide a margin marking environment based more closely on three-dimensional data in the digital model 1032 of a subject. The model view window 1030 may provide a two-dimensional or three-dimensional rendering of the digital model, along with tools and/or controls such as those described above for adding, deleting, or otherwise manipulating points 1034 and/or groups of points to mark a margin line 1036 on a tooth surface. As noted above, each change to a point 1034, along with resulting changes to the margin line 1036 may be used to update display of the points and/or margin line in other windows 1010, 1020, 1040 of the user interface 1000.

The video control window 1040 may be included within the user interface 1000 to provide for user selection of a still image for display in the video image window 1010, or more generally for navigating within a video stream captured by the camera system. Using the video control window 1040, a user may navigate within the video sequence as appropriate to create, inspect, and validate a margin line. The video sequence may be a video sequence from a camera system used to obtain three-dimensional data for a scan subject, or from a related camera having a substantially known relationship relative to the camera system and/or scan subject.

In one embodiment, the controls may include a number of thumbnail images 1042 showing images from various camera locations during a scan. Other visual cues may be provided with the thumbnail images 1042. For example, an arrow 1044 or other highlighting feature may be provided to illustrate which of the thumbnail images 1042 contain surface area visible in the model view window 1030, or which of the thumbnail images 1042 contain visible portions of the margin line. Thumbnail images 1042 may also or instead by displayed with orientation information. For example, the thumbnail images 1042 may provide orientation details (e.g., buccal, lingual, distal, mesial) or distance by providing annotations using text, icons, or other visual cues contained with or displayed adjacent to each thumbnail. A current video image displayed in the video image window 1010 may also be identified using highlighting 1046 or other visible indicia.

While the current image is depicted at a left-hand side of the window 1040, the current image may instead be positioned at the center of the thumbnail images 1042 or any other suitable location. It will be appreciated that thumbnail images 1042 may in general be selected and/or grouped according to relevance in order to assist a user. For example, thumbnail images 1042 may be selected to provide a variety of views of a current tooth, or of a portion of a margin line currently being edited. Where a dentist (or other scanner) has identified a number of teeth, grouping the thumbnails so that only images of the current tooth may be particularly helpful to a downstream technician.

While a one-dimensional thumbnail array is depicted in FIG. 10, it will be understood that numerous other techniques are known in the art for video timeline control and may be suitably employed with the systems described herein. By way of example and not of limitation, the video control window 1040 may display a two-dimensional array (i.e., 2×5, 3×5, or any other suitable dimensions). The window 1040 may also, or instead, include a slider or other control for user navigation along an entire video sequence. In another aspect, the thumbnail images 1042 may be temporally adjacent frames of video data, or may be spaced apart at suitable intervals such as every fifth frame of data, tenth frame of data, or the like. The thumbnail images 1042 may also, or instead, include synthesized images from a variety of viewpoints useful for margin marking. These and other variations may be usefully employed within the video control window 1040 described herein.

In one aspect a perspective or point of view may be synchronized between the video image window 1010 and the model view window 1030. For example, a user may operate controls within the video control window 1040 to select a video image for display in the video image window 1010. In response to selection of a video image of a subject, the model view window 1030 may render the subject (based upon a digital model of the subject) from the same point of view or perspective. To this end, position data for the scanner/camera, such as x, y, and z position (in any coordinate system referenced to the subject) and rotational orientation, may be obtained from data acquired during the scan. This position data may then be employed to render the digital model appropriately.

A user may also or instead control the perspective of the digital model in the model view window 1030 as generally described above. In this case, the video image window 1010 may be updated to provide a video image more closely corresponding to the user-selected perspective in the model view window 1030. A number of techniques may be suitable employed for synchronization from the model view window 1030 to the video image window 1010. For example, user controls for altering perspective in the model view window 1030 may be constrained so that a user can only move perspective along the camera path that was used to obtain the three-dimensional data. In this example, a limited ability to pan or zoom may be provided for variations in point of view that stay within the context of the current video image. In addition, the video image may be warped, re-sized, or otherwise manipulated to accommodate minor variations in rotational orientation or the like. As another example, a new video image may be selected for display in the video image window 1010 by finding a video image within the full video sequence (or a portion of the full video sequence) that most closely corresponds to the user-selected viewpoint. This may be determined, for example based upon any suitable distance or other quantitative comparison between position and/or rotational orientation of a new user-select viewpoint and viewpoints associated with images within the video sequence. As another example, a new video image may be synthesized that nearly or exactly corresponds to the user-selected perspective using various combinations of video data, camera system distortion models, three-dimensional digital model data, and any other available data. This may include, for example, mapping video texture data onto the three-dimensional model, or combining video data from a number of different video images, along with suitable warping, scaling, registration, and the like.

In another embodiment, the system may provide unidirectional synchronization. That is, the model view may respond to a selection of a still image by rendering from the perspective of the selection. The model view may subsequently be manipulated to provide any suitable perspective for editing or validating a margin, while the still image in the video image window 1010 remains unchanged. The user may be provided with a reset control to return the model view to the perspective of the still image, and the model view may continue to respond to a new image selection by re-rendering the model from the perspective of the new image. Thus views in the video image window 1010 may control rendering in the model view window 1030. However, altering perspective of the model view window 1030 has no effect on the still image displayed in the video image window 1010.

In another aspect, display of the points 1012 in the video image window 1010 may be synchronized with display of points 1032 in the model view window 1030. Thus a user manipulation of a point 1012 in the video image window 1010 may be used to update the same point 1032 in the model view window 1030, and a user manipulation of a point 1032 in the model view window 1030 may be used to update the same point 1012 in the video image window 1010. It will be understood that in either case, a user may select a point in two dimensions (corresponding to the user interface), with a three-dimensional location of the point determined by projecting the x and y coordinate of the point on to a surface of the model or the still image. In either case, information about the camera system such as distortion models for camera channels may be employed to accurately transform spatial information for a point between the two windows 1010, 1030. More generally, some or all of the windows 1010, 1020, 1030, 1040 may include tools for manipulating points and/or the margin line, with any changes updated throughout all of the windows. It will be appreciated that numerous other arrangements may be provided. For example, points and/or margin lines may optionally not be displayed in the video control window 1040 or cross-sectional view window 1020. As another example, tools for controlling points may only be provided in one or two of the windows, such as the video image window 1010 and the model view window 1030.

Using the user interface 1000 and tools described above, a wide array of iterative and/or interactive margin marking processes may be employed. By way of example and not of limitation, one such operation is now described. A user may initiate a margin marking process by selecting a thumbnail image 1042 in the video control window 1040 for display (as a "working image") in a working area such as the video image window 1010. A user may then use a mouse to select points along a margin line in the video image window 1010. The margin marking system may receive these two-dimensional selections through the user interface 1000 and correlate them to the three-dimensional space of the three-dimensional model. Using location/rotation data for the selected image, the system may also render a corresponding view of the digital model in the model view window 1030, along with any corresponding points selected in the working area. A user may review point selections and a corresponding margin line in the model view window 1030. In addition, the user may manipulate the model view to provide any number of useful perspectives on the model for visual validation of the selected margin or points thereof. A user may then select another thumbnail to obtain a new working image, and continue iteratively until adequate points have been identified to derive a complete, closed loop margin line.

In another aspect, tools may be provided for manipulating the digital model, either through interaction with the model in the model view window 1030, the video image in the video image window 1010, or a combination of these. For example, the three-dimensional cursor techniques described above may be more generally applied to address possible variations between a video image (based upon a single image pair) and a model view (based upon a composite of image pairs). The variations may result from image-to-image variations in subject matter clarity, or model-wide variations resulting from the synthesis of numerous different image pairs. In addition, the techniques described above may be used to correct errors originating with the person who originally operated the scanner. For example, where a flap of skin or the like obstructs a portion of a margin, or a particle or the like creates a discontinuity on the margin line, these deficiencies may be addressed by extrapolating, interpolating, or otherwise synthesizing other available surface data either automatically, semi-automatically, or manually using the interactive model editing tools above.

While the invention has been described in connection with certain preferred embodiments, other embodiments may be understood by those of ordinary skill in the art and are encompassed herein.

What is claimed is:

1. A method comprising:
   creating a three-dimensional model with a processor from a sequence of image sets stored in a memory, each image set including a plurality of images of a subject including dentition, each one of the plurality of images captured from a different optical axis, the plurality of images including at least one video image;
   rendering the three-dimensional model in a user interface of a display from a perspective;
   automatically selecting a video image with the processor from the sequence of image sets that contains a view of the subject most closely corresponding to the perspective;
   displaying the video image in the user interface of the display concurrently with the three-dimensional model; and
   providing a tool with the processor in the user interface for marking a margin of the dentition.

2. A system comprising:
   a memory storing a three-dimensional model of a subject and a sequence of image sets used to create the three-dimensional model, each image set including a plurality of images of a subject including dentition, each one of the plurality of images captured from a different optical axis, the plurality of images including at least one video image;
   a display configured to provide a user interface presenting the sequence of image sets; and
   a processor configured to render the three-dimensional model in the user interface from a perspective, select a video image from the sequence of image sets that contains a view of the subject most closely corresponding to the perspective, display the video image in the user interface concurrently with the three-dimensional model, and provide a tool for marking a margin of the dentition.

3. A method comprising:
creating a three-dimensional model with a processor from a sequence of image sets stored in a memory, each image set including a plurality of images of a subject, each one of the plurality of images in each image set captured from a different optical axis;
displaying one of the plurality of images in a first window of a display;
rendering the three-dimensional model with the processor in a second window of the display; and
synchronizing the first window and the second window with the processor to provide a common perspective on the subject for both the three-dimensional model and the one of the plurality of images.

4. The method of claim 3 further comprising receiving a user selection of a different one of the plurality of images and rotating the three-dimensional model to maintain the common perspective.

5. The method of claim 3 further comprising receiving a user selection of a different one of the plurality of images and translating the three-dimensional model to maintain the common perspective.

6. The method of claim 3 further comprising receiving a user selection of a different one of the plurality of images and scaling the three-dimensional model to maintain the common perspective.

7. The method of claim 3 further comprising receiving a user selection of a different perspective of the three-dimensional model and selecting a new one of the plurality of images to maintain the common perspective.

8. The method of claim 3 further comprising receiving a user selection of a different perspective of the three-dimensional model and creating a composite video image from two or more of the plurality of images to provide a common perspective on the subject.

9. A system comprising:
a memory storing a three-dimensional model of a subject and a sequence of image sets used to create the three-dimensional model, each image set including a plurality of images of a subject, each one of the plurality of images in each image set captured from a different optical axis;
a display configured to provide a user interface displaying one of the plurality of images in a first window; and
a processor configured to render the three-dimensional model in a second window displayed in the user interface concurrently with the one of the plurality of images in the first window and to synchronize the first window and the second window to provide a common perspective on the subject in both the three-dimensional model and the one of the plurality of images.

10. The system of claim 9 wherein the processor is configured to receive a user selection of a different one of the plurality of images and rotate the three-dimensional model to maintain the common perspective.

11. The system of claim 9 wherein the processor is configured to receive a user selection of a different one of the plurality of images and translate the three-dimensional model to maintain the common perspective.

12. The system of claim 9 wherein the processor is configured to receive a user selection of a different one of the plurality of images and scale the three-dimensional model to maintain the common perspective.

13. The system of claim 9 wherein the processor is configured to receive a user selection of a different perspective of the three-dimensional model and select a new one of the plurality of images to maintain the common perspective.

14. The system of claim 9 wherein the processor is configured to receive a user selection of a different perspective of the three-dimensional model and create a composite video image from two or more of the plurality of images to provide a common perspective on the subject.

15. A method comprising:
displaying a three-dimensional model of dentition from a perspective in a display;
providing a plurality of video images of the dentition in a memory;
automatically selecting one of the plurality of video images with the processor that shows the dentition from the perspective; and
displaying the one of the plurality of video images in a user interface of the display concurrently with the three-dimensional model as an aid to visually determining a margin of the dentition.

16. The method of claim 15 further comprising displaying a margin on one or more of the three-dimensional model or the one of the plurality of video images.

17. The method of claim 16 further comprising receiving a user modification of the margin and updating the display with a modified margin.

18. A system comprising:
a display having a window for displaying a three-dimensional model of dentition from a perspective;
a camera providing a plurality of video images of the dentition; and
a processor configured to select of one of the plurality of video images that shows the dentition from the perspective and display in a second window in the display the one of the plurality of video images concurrently with the three-dimensional model as an aid to visually determining a margin of the dentition.

19. The system of claim 18 wherein the processor is configured to display a margin on one or more of the three-dimensional model or the one of the plurality of video images.

20. The system of claim 19 wherein the processor is configured to receive a user modification of the margin and update the display with a modified margin.

* * * * *